United States Patent
Patel et al.

(10) Patent No.: US 11,857,425 B2
(45) Date of Patent: *Jan. 2, 2024

(54) SYSTEM AND METHOD FOR MAKING PERSONALIZED FIBROCARTILAGE IMPLANTS

(71) Applicant: Rutgers, The State University of New Jersey, New Brunswick, NJ (US)

(72) Inventors: Jay M. Patel, Montville, NJ (US); Michael G. Dunn, Manalapan, NJ (US); Charles J. Gatt, Skillman, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 116 days.

This patent is subject to a terminal disclaimer.

(21) Appl. No.: 17/502,409

(22) Filed: Oct. 15, 2021

(65) Prior Publication Data
US 2022/0031463 A1 Feb. 3, 2022

Related U.S. Application Data

(63) Continuation of application No. 15/781,238, filed as application No. PCT/US2016/062805 on Nov. 18, 2016, now Pat. No. 11,154,403.
(Continued)

(51) Int. Cl.
A61F 2/38 (2006.01)
A61B 34/10 (2016.01)
(Continued)

(52) U.S. Cl.
CPC ............ *A61F 2/3872* (2013.01); *A61B 34/10* (2016.02); *A61F 2/30942* (2013.01);
(Continued)

(58) Field of Classification Search
CPC ................... A61F 2/3872; A61F 2/442; A61F 2002/30069; A61F 2002/302;
(Continued)

(56) References Cited

U.S. PATENT DOCUMENTS

| 5,465,323 A | 11/1995 | Mallet |
| 5,594,651 A | 1/1997 | St. Ville |

(Continued)

FOREIGN PATENT DOCUMENTS

| CN | 103796609 A | * | 5/2014 | ............. A61B 34/10 |
| CN | 103796609 A | | 5/2014 | |

(Continued)

OTHER PUBLICATIONS

Chantarapanich et al: "Scaffold Library for Tissue Engineering: A Geometric Evaluation", Computational and Mathematical Methods in Medicine, Jun. 12, 2012, [retrieved on Dec. 31, 2016] Retrieved from internet: <https://www.hindawi.com/journals/cmmm/2012/407805/>.

*Primary Examiner* — Cedric Johnson
(74) *Attorney, Agent, or Firm* — FOX ROTHSCHILD LLP

(57) ABSTRACT

Systems (500, 1000) and methods (1700) for fabricating a soft tissue implant (100, 400). The methods generally involve: receiving implant data representative of the target implant; determining a planned weaving path for forming the soft tissue implant; and communicating the planned weaving path to an output device.

19 Claims, 17 Drawing Sheets

Related U.S. Application Data

(60) Provisional application No. 62/262,544, filed on Dec. 3, 2015.

(51) Int. Cl.
  *A61F 2/30* (2006.01)
  *A61F 2/44* (2006.01)

(52) U.S. Cl.
  CPC ........ *A61F 2/442* (2013.01); *A61B 2034/102* (2016.02); *A61F 2002/302* (2013.01); *A61F 2002/30069* (2013.01); *A61F 2002/30952* (2013.01); *A61F 2002/4495* (2013.01)

(58) Field of Classification Search
  CPC .... A61F 2002/30952; A61F 2002/4495; A61F 2/30942; A61B 34/10; A61B 2034/102
  USPC ............................................................ 703/1

See application file for complete search history.

(56) References Cited

U.S. PATENT DOCUMENTS

| | | | |
|---|---|---|---|
| 2004/0133275 | A1* | 7/2004 | Mansmann ......... A61F 2/30965 623/23.51 |
| 2009/0076371 | A1 | 3/2009 | Lang et al. |
| 2009/0196901 | A1 | 8/2009 | Guilak et al. |
| 2011/0093073 | A1* | 4/2011 | Gatt .................... A61F 2/30756 623/23.72 |
| 2011/0287122 | A1 | 11/2011 | Kim et al. |
| 2013/0238096 | A1 | 9/2013 | Kotlus |
| 2013/0253646 | A1* | 9/2013 | Altman ................. A61F 2/0063 623/8 |
| 2014/0066935 | A1 | 3/2014 | Fitz et al. |
| 2014/0244220 | A1* | 8/2014 | McKinnon ............... A61F 2/02 703/1 |
| 2015/0086607 | A1 | 3/2015 | Johnson et al. |
| 2015/0198943 | A1 | 7/2015 | Kotlus |

FOREIGN PATENT DOCUMENTS

| | | | |
|---|---|---|---|
| JP | 2009056299 A | 3/2009 | |
| WO | 2009/149093 A1 | 12/2009 | |
| WO | 2015/089118 A1 | 6/2015 | |
| WO | WO-2015089118 A1 * | 6/2015 | ........... A61B 17/688 |

* cited by examiner

SYSTEM AND METHOD FOR MAKING PERSONALIZED FIBROCARTILAGE IMPLANTS

CROSS-REFERENCE TO RELATED APPLICATIONS

The present application is a continuation of U.S. Non-provisional patent application Ser. No. 15/781,238, filed Jun. 4, 2018, which will issue on Oct. 26, 2021 as U.S. Pat. No. 11,154,403, and is the U.S. National Phase of International Patent Application Serial No. PCT/US16/62805, filed Nov. 18, 2016, which claims the benefit of U.S. Provisional Ser. No. 62/262,544, filed on Dec. 3, 2015. The entire disclosures of the applications noted above are incorporated herein by reference.

FIELD OF THE INVENTION

This invention relates to systems and methods for manufacturing fibrocartilage and, in particular, to a system and method for personalizing the structure of the implant and forming the implant.

BACKGROUND

Meniscus injuries are common in the general population due to workplace accidents and sports related activities, with rates ranging from approximately 60 to 70 incidences per 100,000 individuals. Approximately 1.5 million knee arthroscopic procedures were performed, with more than 50% involving meniscal surgery. Few alternative treatment options exist for extensive meniscal loss. One is meniscal allograft transplantation. While this procedure has shown promising short-term results, long-term results are inconsistent due to poor tissue remodeling. Also, it is difficult to obtain the allograft matching the size of the damaged meniscus from tissue banks due to the shortage of available meniscal allografts. Correct sizing of the meniscal allograft is important for load transfer and healing; a meniscus that is too small may increase hoop stresses on the graft and a meniscus that is too large can increase forces on the articular cartilage and may over-stuff the knee.

Another alternative treatment is the use of biocompatible, resorbable scaffolds to replace damaged meniscal tissue. In this case, the following have been designed: a clinically useful meniscus replacement device with a fiber-reinforced meniscus scaffold having an intricate internal shape that can bear circumferential tensile loads. The strength of the scaffold is due to the many intersecting fiber reinforcements that distribute weight throughout the structure. This artificial weight-bearing tissue has a great potential in treating meniscus injuries.

However, there are still two major technical challenges associated with this treatment: designing personalized fiber-reinforced scaffolds and fabricating personalized scaffolds with consistent quality. For example, scaffolds can be fabricated to meet the patient's needs in his/her profession such as those needed to withstand high impact energy for athletes. The current fabrication process is labor-intensive and requires manual weaving of a continuous fiber in distinct patterns. This manual process only allows fabricating a limited type of meniscus size and weaving patterns and thus is not capable of personalizing the artificial meniscus matching the geometry of a native meniscus. In addition, this fabrication process is limited to lab processes. The quality of the scaffold is difficult to control and is subject to human errors. The meniscus scaffold quality depends heavily on the expertise of the operators handling the samples. Manufacturing and fabricating the fiber-reinforced meniscus scaffold can yield inconsistent results due to inter- and intra-operator variability which makes the process irreproducible. There is a clear need to develop a methodology that addresses the above two technical challenges.

SUMMARY

The present disclosure concerns systems and methods for fabricating a soft tissue (e.g., a fibrocartilage tissue) implant, and the implant fabricated using the same. The methods comprise: receiving, by a processor, first data specifying at least one soft tissue dimension (e.g., a length such as an Anterior-to-Posterior ("AP") compartment length and/or a width such as a Medial-to-Lateral ("ML") compartment width), and a weighting factor W; using, by the processor, the first data to generate second data defining a target soft tissue implant comprising a scaffold designed to replace a biological soft tissue in a subject and a reinforcing matrix designed to provide structural support to the scaffold; transforming, by the processor, the first data into a plurality of node location coordinates in a multi-dimensional space which specify a node configuration for a base surface that is to be used in subsequent weaving or printing operations to fabricate the soft tissue implant; using, by the processor, the plurality of node locations to determine a planned weaving or printing path for forming an interlaced fibrous structure having a shape based on a shape of the target soft tissue implant; and communicating information defining the planned weaving or printing path from the processor to an external output device for facilitating performance of the subsequent weaving or printing operations resulting in the fabrication of the soft tissue implant. Optionally, the implant may be a meniscal replacement device or an intervertebral disc replacement device.

In some such scenarios, the external output device is a weaving machine which forms the interlaced fibrous structure in accordance with the planned weaving path. Alternatively or additionally, the external output device is a display or printer. Optionally, the methods may also include injecting a scaffold material into the interlaced fibrous structure to form the implant.

In those or other scenarios, the methods also involve optimizing the weighting factor W based on soft tissue dimensions or sub-tissue dimensions (i.e., an actual anterior width, an actual posterior width, and an actual body width). The weighting factor W is optimized using a root-mean-square error algorithm to identify a value that minimized an error between desired implant widths and actual implant widths in an anterior region, a posterior region and a body region. An example of a root-mean-square error algorithm is defined by the following Mathematical Equation $$RMSError = \sqrt{(ANT_{des} - ANT_{act})^2 + (BOD_{des} - BOD_{act})^2 + (POS_{des} - POS_{act})^2}$$

where RMSError represents a root-mean-square error, $ANT_{des}$ represents a desired anterior width, $ANT_{act}$ represents an actual anterior width, $BOD_{des}$ represents a desired body width, $BOD_{act}$ represents an actual body width, $POS_{des}$ represents a desired posterior width, and $POS_{act}$ represents an actual posterior width.

In at least some such scenarios, the fabrication of the implant may also include forming an anterior attachment point by a first fiber of the interlaced fibrous structure that exits from an anterior end of the scaffold and forming a posterior attachment point by a second fiber of the interlaced fibrous structure that exits from a posterior end of the scaffold. The anterior attachment point and the posterior attachment point are configured for attachment of the implant to surrounding tissue. Optionally, the first fiber and the second fiber may have different lengths.

The weighting factor W may be optimized to introduce asymmetry into a shape of the implant. Alternatively and/or additionally, an asymmetrical weaving pattern may be selected from a database when the implant is configured to replace a knee meniscus while determining the planned weaving or printing path for forming the interlaced fibrous structure.

Optionally, the weighting factor Walters a spacing between the node location coordinates to introduce asymmetry into a shape of the implant.

In those or yet other scenarios, the processor: simulates the subsequent weaving operations using the planned weaving path to generate a simulated articulating surface; superimposes the simulated articulated surface into an image of soft tissue to be replaced by the soft tissue implant; and adjusts the planned weaving path based on an analysis of results of said superimposing.

In certain other scenarios, disclosure concerns systems and methods for fabricating a soft tissue (e.g., a fibrocartilage tissue) implant, and the implant fabricated using the same. The methods comprise: receiving first data specifying at least a tissue dimension and a weighting factor W, using the first data to generate second data defining the implant, the second data comprising a reinforcing matrix formed from an interlaced fibrous structure and designed to provide structural support to a scaffold, transforming the first data into a plurality of node location coordinates in a multi-dimensional space which specify a node configuration for a base surface used in subsequent weaving operations for forming the interlaced fibrous structure, the interlaced fibrous structure having a shape corresponding to a shape of the implant, using the plurality of node locations to determine a planned weaving or printing path for forming the interlaced fibrous structure, and communicating information defining the planned weaving or printing path to an external output device for facilitating performance of the subsequent weaving or printing operations resulting in the fabrication of the interlaced fibrous structure.

In one or more such scenarios, the methods may also include optimizing the weighting factor W based on at least one an actual anterior width, an actual posterior width, and an actual body width, the optimizing comprising using a root-mean-square error algorithm to identify a value that minimizes an error between desired implant widths and actual implant widths in an anterior region, a posterior region and a body region. Optionally, the weighting factor W is optimized to introduce asymmetry into a shape of the implant. Additionally and/or alternatively, the weighting factor W may alter a spacing between the node location coordinates to introduce asymmetry into a shape of the implant.

BRIEF DESCRIPTION OF THE FIGURES

The present solution will be described with reference to the following drawing figures, in which like numerals represent like items throughout the figures.

DETAILED DESCRIPTION

Figure 1:
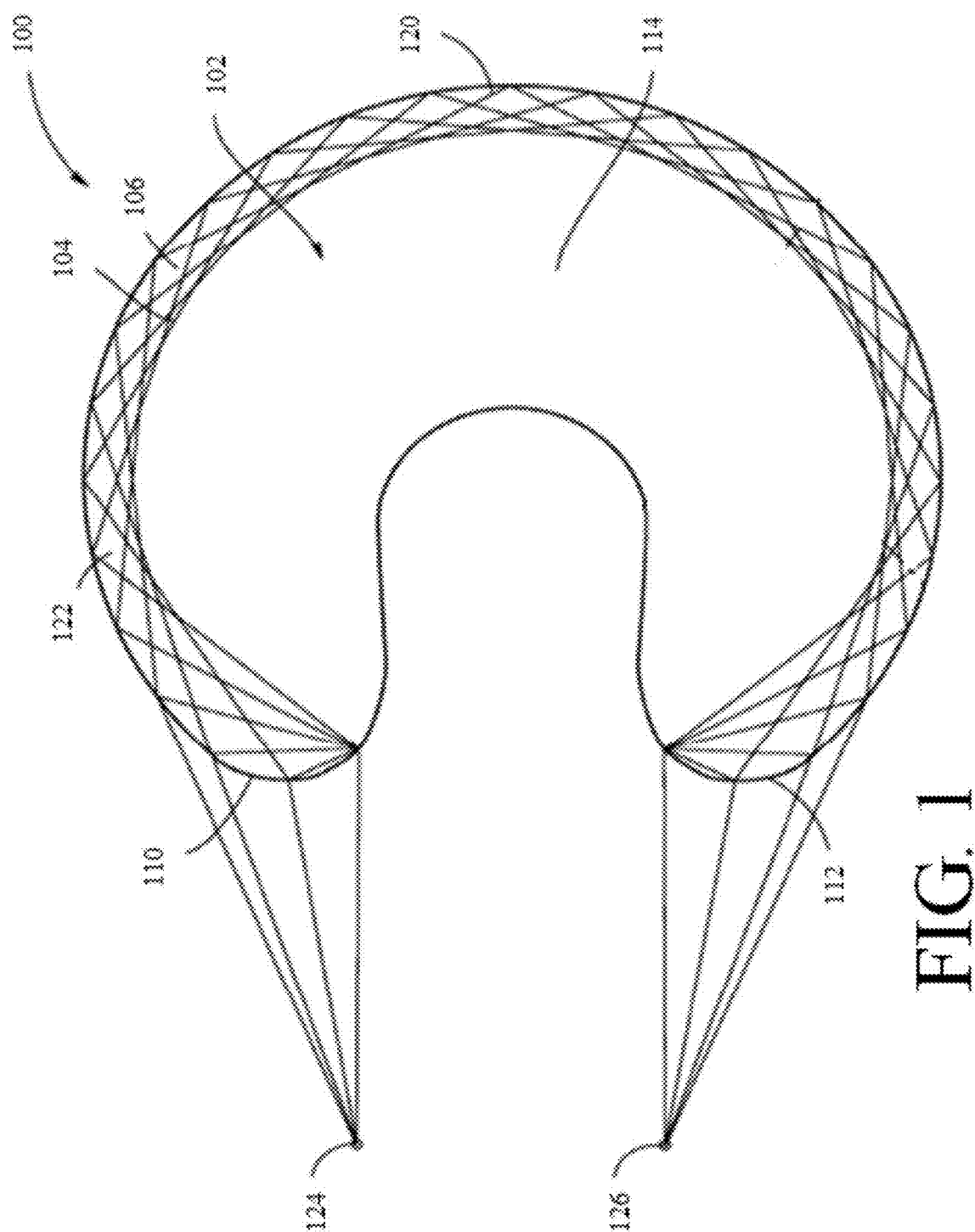
FIGS. 1 and 2 are top views of an exemplary implant with a first exemplary reinforcing matrix.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

The system and method of making a personalized implant will be described herein with respect to making of a knee meniscus implant. Although the instant implant is described in relation to making of a knee meniscus implant, the teachings of the instant disclosure may also be applied to making implants for replacing other tissues similar in nature and function to the meniscus, such as intervertebral discs, temporomandibular discs, wrist menisci, and the like. These tissues are similar to the knee meniscus in that they are composed of fibrocartilage and function as load transmitters and distributors to prevent high-stress cartilage-on-cartilage or bone-on-bone contact that is detrimental to the joint. It will also be understood that the instant teachings may be applied to make implants for both human and animal patients.

Exemplary implants will be described with reference to FIGS. 1-4C. Referring to FIG. 1, there is shown an implant 100 comprising a scaffold 102 and reinforcing matrix 120 embedded in or coupled to the scaffold 102. The scaffold 102 generally comprises a material that has been engineered to cause desirable cellular interactions to contribute to the formation of new functional tissues for medical purposes and/or the replacement of portions of or whole biological tissues. The reinforcing matrix 120 is an engineered structure generally configured to strengthen and/or support the scaffold. As such, the reinforcing matrix 120 may also have the same general shape and geometry as the scaffold 102, but with a greater density of material (e.g., fiber) as compared to that of the scaffold 102. The material can include, but is not limited to, natural materials, synthetic materials, biodegradable materials and permanent materials. The increased density causes the reinforcing matrix 120 to be stiffer than the scaffold 102 such that the reinforcing matrix 120 provides structure support to the scaffold 102. The structural support can include, but is not limited to, tensile support and/or compressive support.

In some scenarios, the porosity of the implant 100 is designed in accordance with a particular application. For example, the implant 100 is designed to have a relatively high porosity to ensure adequate tissue and cell infiltration therethrough. Any level of porosity can be used herein without limitation provided that is sufficient for facilitating adequate cell seeding, fluid flow and structural integrity.

In some scenarios, the implant 100 is used as a fibrocartilage implant (e.g., a knee meniscus, intervertebral disc and/or TMJ joint implant), a tendon implant, a ligament implant and/or cartilage implant. The shape and geometry of the scaffold 102 (and consequently the implant) is based on the shape and geometry of the soft tissue in need of replacement. Thus, in the case of a meniscus implant, the scaffold 102 may be constructed as a c-shaped disc with a wedge-like cross-section (similarly to a knee meniscus). Furthermore, the scaffold 102 may be shaped concave on the top (which would come in contact with a femur) and flat on the bottom (which would rest on the tibial plateau).

Figure 2:
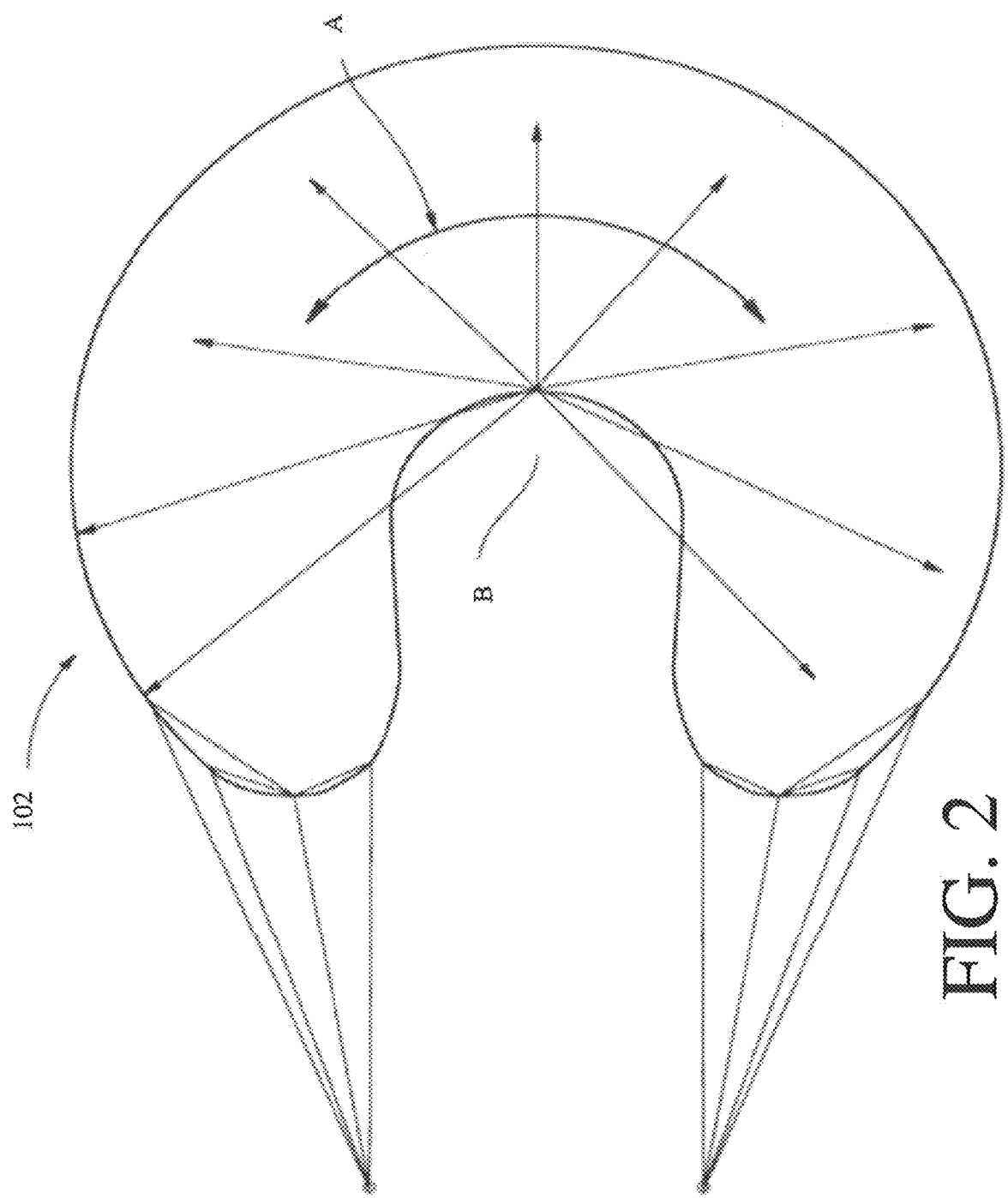

The scaffold 102 includes an anterior end 110, a posterior end 112 and a middle section 114 defining a path between the anterior end 110 and the posterior end 112. In a meniscus replacement scenario, the middle section 114 is essentially arc-shaped and defines a curved path between the anterior and posterior ends 110, 112. Referring to FIGS. 1-2, for the purposes of the instant disclosure, the circumferential direction of the scaffold 102 is indicated by arrow A and generally extends along the middle section 114 of the scaffold 102.

Referring back to FIG. 1, the reinforcing matrix 120 may be formed by at least one fiber 122 extending between the anterior end 110 and posterior end 112 of the scaffold 102 and exiting each end to form an anterior attachment point 124 and a posterior attachment point 126. As used herein, the term "fiber" refers to any generally elongated member consisting of a single component (e.g., monofilament suture) or multiple components (e.g., multifilament suture). The physical property of the fiber 122 (such as tensile strength, cross-sectional area, diameter, flexibility, etc.) may vary over the length of the fiber 122. In some scenarios, multiple fibers may be used to form the reinforcing matrix 120. The fibers may be made of the same or different materials and may follow the same or different paths.

Preferably, at least a portion of the fiber 122 forming the reinforcing matrix 120 is positioned substantially in circumferential direction 104. In some scenarios, the fiber 122 forming the reinforcing matrix 120 may be arranged in two (2) different arrangements: the circumferential arrangement 104; and an orthogonal arrangement 106. As used herein, the terms "orthogonal arrangement" and "arranged orthogonally" mean an arrangement of fibers extending in directions substantially parallel to arrows B in FIG. 2 at various angles in relation to the scaffold 102.

Figure 3:
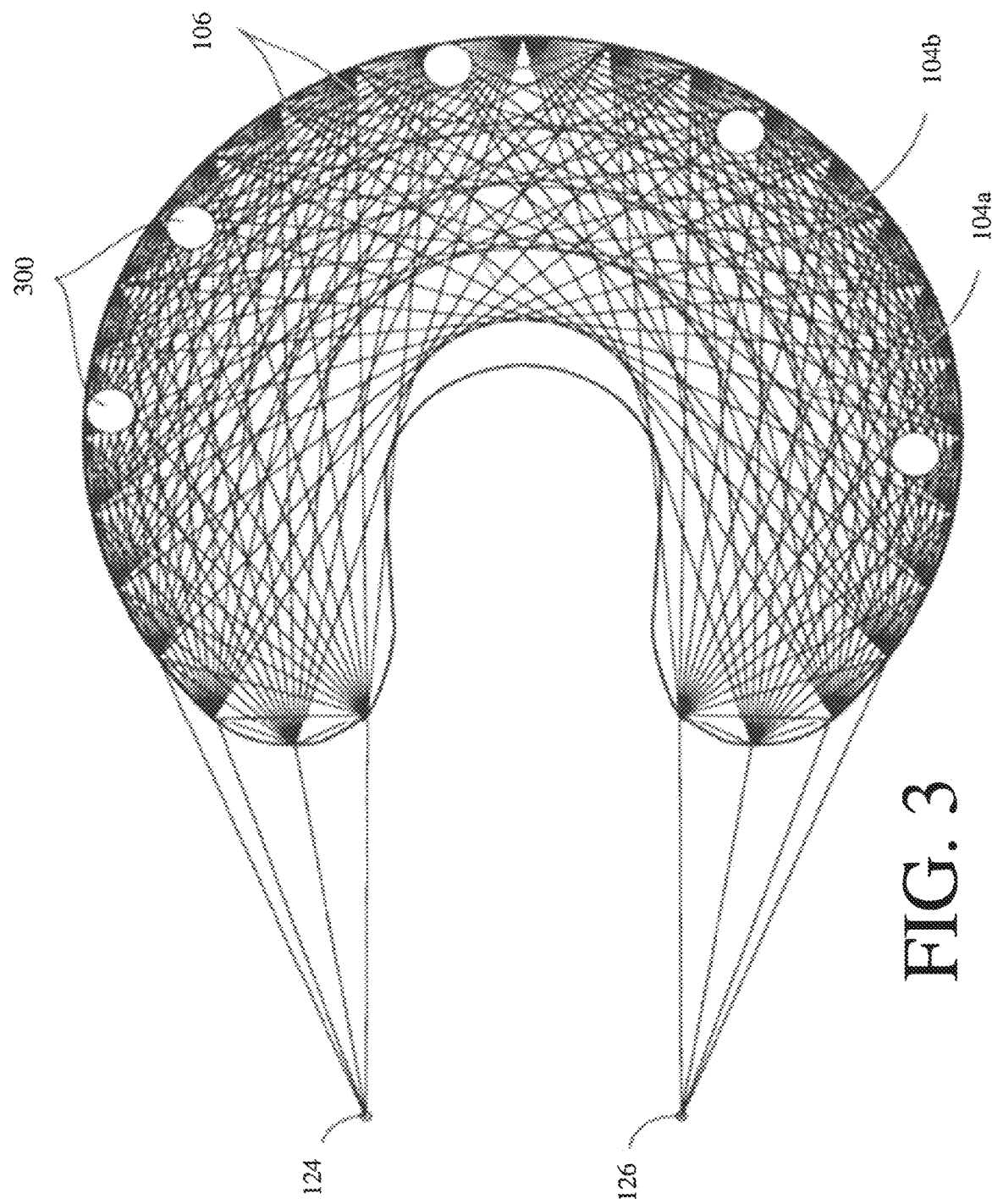
FIG. 3 is a top view of an exemplary implant with a second exemplary reinforcing matrix.

In reference to FIG. 3, the reinforcing matrix 120 comprises one or more circumferential fibers 104a, 104b (collectively referred to as "104") and one or more orthogonal fibers 106. The term "circumferential fiber" refers to a fiber that extends between the anterior end 110 and posterior end 112 of the scaffold 102 along the middle section 114 of the scaffold 102 and is positioned at least in part substantially parallel to the circumferential axis. The term "orthogonal fibers" refers to fibers that cross the circumferential fibers at various angles to keep them from separating. Keeping the circumferential fibers from separating increases the durability and longevity of the implant. For convenience, terms "circumferential fiber network" and "orthogonal fiber network" may be used herein to refer to multiple circumferential fibers or multiple orthogonal fibers, respectively.

In operation, the compressive force on the implant 1 in the axial direction is translated into tensile hoop stresses in the circumferential direction. The hoop stresses propagate along the circumferential fibers 104. In vivo, as meniscal tissue grows into the implant 1 and cells attach to the fiber networks, cells on or about the circumferential fibers 104 experience the same mechanical environment as in a normal meniscus, resulting in the formation of tissue with the essentially the same organization and directionality of collagen fibers as the original meniscus. The reinforcing matrix 120 may be formed with one single continuous fiber arranged both circumferentially and orthogonally. Alternatively, the reinforcing matrix 120 may be formed using multiple fibers. In such scenarios, the circumferential fibers 104 as well as orthogonal fibers 106 may be formed by the same or different strands of fiber or a combination thereof.

As noted above, the implant 1 includes an anterior attachment point 124 and a posterior attachment point 126 for attaching the implant to tissue adjacent to the implantation site. These attachment points are formed by fiber exiting from the anterior and posterior ends 124, 122 of the scaffold 102, respectively. Moreover, in some scenarios, the implant 100 may comprise one or more additional attachment points 300 formed in the middle section 114 of the scaffold 102. For example, the additional attachment points 300 are formed on the exterior periphery of the middle section 114. Such attachment points 300 are referred to as peripheral attachment points. In some scenarios, the peripheral attachment points coincide with points at which orthogonal fibers cross circumferential fibers.

As noted above, intervertebral discs or temporomandibular joint discs function as load transmitters and distributors to prevent high-stress bone-on-bone contact. For example, an intervertebral disc comprises the annulus fibrosus and the nucleus pulposus. The nucleus pulposus is the inner gelatinous material surrounded by the annulus fibrosus. The nucleus pulposus distributes mechanical loads placed upon the disc, while the annulus fibrosus provides structural integrity and constrains the nucleus pulposus to a specific spinal region. The annulus fibrosus has an internal structure which is very similar to the internal structure of meniscal tissue. Accordingly, torroidal concepts herein described may be utilized to construct implants for full or partial replacement of annulus fibrosus.

Figure 4A:
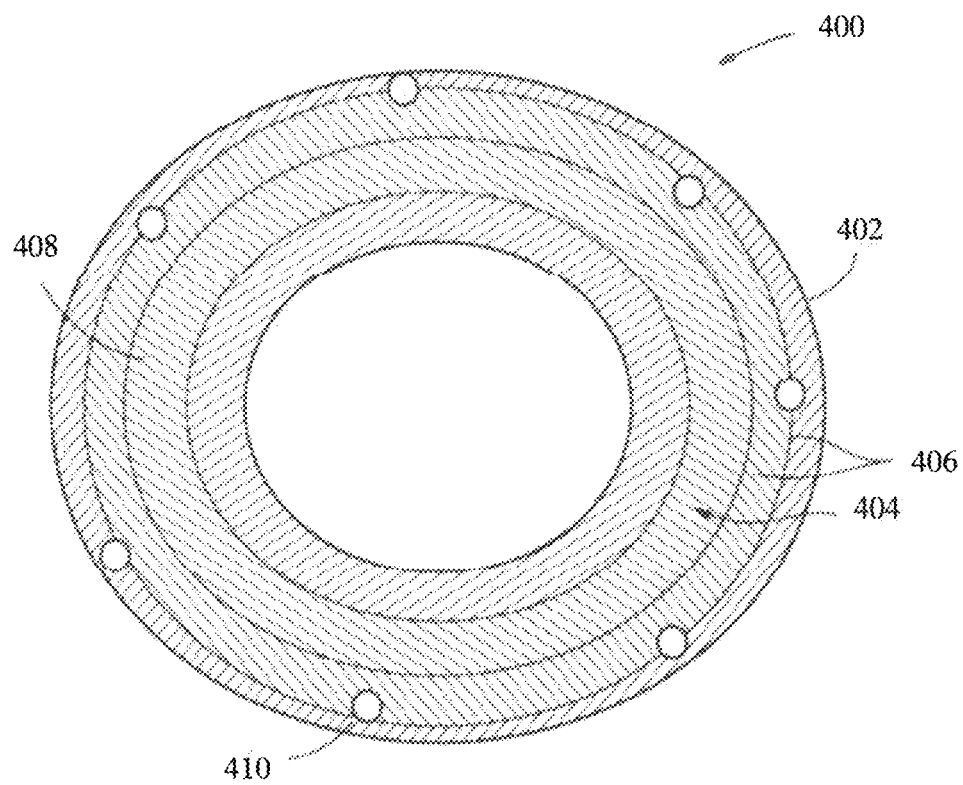
FIG. 4A is a top view of an implant comprising a toroidal-shaped scaffold and a reinforcing matrix.

Referring to FIG. 4A, an implant 400 may comprise a torroidal-shaped scaffold 402 and a reinforcing matrix 404. The reinforcing matrix 404 may be constructed as is described above in reference to meniscus implants. In some scenarios, the reinforcing matrix 404 comprises circumferential fibers 406 and orthogonal fibers 408. The orthogonal fibers 408 cross the circumferential fibers 406 to prevent separation of the circumferential fibers 406. However, in contrast to other scenarios (such as those described above), the fibers forming the reinforcing matrix 404 do not exit the scaffold 402 and the implant 400 may be secured by attaching the implant 400 to the healthy tissues at peripheral attachment points 410.

Figure 4B:
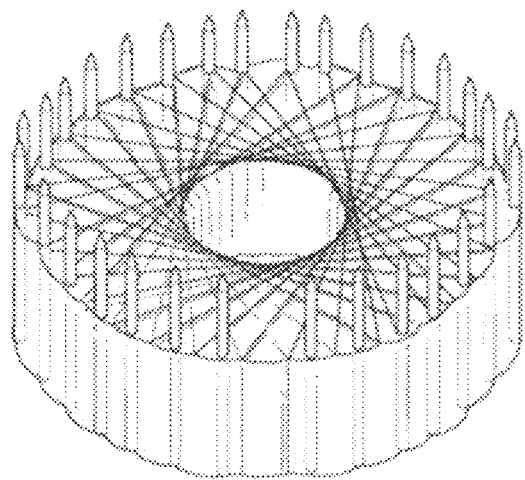
FIGS. 4B and 4C are elapsed time perspective views of the implant shown in FIG. 4A as the fiber(s) is(are) being wound.
Figure 4C:
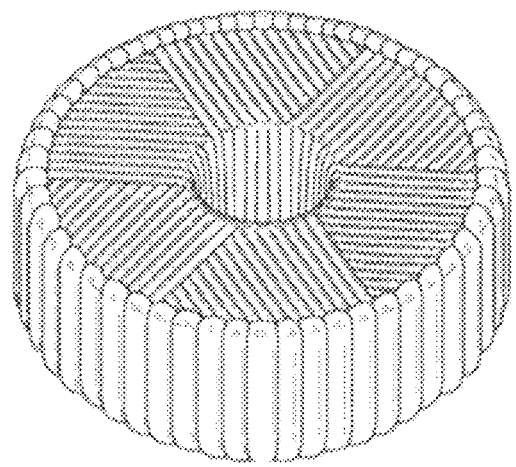

The implant 400 in the process of being wound is depicted in FIGS. 4B and 4C. The implant 400 may be fabricated in the shape of a vertebral disc, wherein the torroidal-shaped scaffold 402 defines an interior cavity filled with a biocompatible material with physical properties equivalent to the properties of the nucleus pulposus of a patient's vertebral disc. Alternatively, the implant 400 is configured to replace only the annulus fibrosus or a part of the annulus fibrosus.

For both the arcuate and torroidal implant constructs, both the scaffold and the reinforcing circumferential and orthogonal matrix fibers may be constructed of naturally-occurring or synthetic biocompatible materials or a combination thereof so to enable infiltration, attachment and proliferation of cells from surrounding tissues once the implant is in place. The naturally-occurring or synthetic biocompatible materials may also be bioresorbable. The scaffold and the reinforcing matrix fibers may be constructed from the same material or different materials and may be fully or partially biodegradable and may have the same or different rate of degradation.

As used herein, the term "synthetic polymer" refers to polymers that are not found in nature, even if the polymers are made from naturally occurring biomaterials. The term "natural polymer", as used herein, refers to polymers that are naturally occurring. The term "biocompatible", as used herein, refers to materials that, in the amounts employed, do not elicit a detrimental response in the host. The term "biocompatible", as used herein, is intended to include materials that may cause some inflammation, tissue necrosis or other immune responses when introduced into the host, provided that these effects do not rise to the level of pathogenesis. The term "bioresorbable", as used herein, refers to those materials that when placed in a living body at standard physiological conditions are degraded through either enzymatic, hydrolytic or other chemical reactions or cellular processes into by-products that are either integrated into or expelled from the body. It is recognized that in the literature, the terms "bioresorbable," "resorbable", "absorbable", "bioabsorbable" and "biodegradable" are frequently used interchangeably and such interchangeable meaning is intended for the present application. In some scenarios, the implant 100, 400 is formed from biodegradable material or materials. The polymers for the instant implant 100, 400 are selected so the implant possesses mechanical properties which are the same or substantially similar to the mechanical properties of the native tissue being replaced.

Examples of suitable natural polymers include, but are not limited to, collagen, hyaluronic acid, fibrin glue, bone marrow, chitosan, alginates, celluloses, starches, silk, elastin, and other animal- or plant-derived proteins or polysaccharides. Suitable synthetic polymers include, but are not limited to, poly(alpha-hydroxy acids), poly(lactide-co-glycolide) (PLGA), poly(L-lactides) (PLLA), polylactides (PLA), polyglycolides (PGA); polyethylene, polypropylene, polyvinyl alcohol (PVA), polyethylene oxide (PEO); poly-p-dioxanone (PDO); polyarylates, polyacrylates, polycarbonates, polyesters, polycaprolactone (PCL) and combinations thereof. Suitable polyarylates and polycarbonates include, but are not limited to the tyrosine-derived polyarylates and polycarbonates disclosed by U.S. Pat. Nos. 5,099,060, 5,198,507, 5,216,115, 5,587,507, 5,658,995 and 6,048,521 (the disclosures of all of which are incorporated herein by reference).

In some scenarios, the scaffold 402 is an amorphous structure composed primarily of Type I collagen. In addition to collagen, other types of materials may be added to alter the scaffold's properties as necessary or desired. For example, other proteins or proteoglycans may be used, including, but not limited to, glycosaminoglycans such as chondroitin sulfate, keratan sulfate, dermatan sulfate, heparin, heparin sulfate and hyaluronic acid. The percentage of these materials in the scaffold may range between zero (0) and about twenty percent (20%) of the dry weight of the scaffold. The fiber for the reinforcing matrix may preferably be made from a bioresorbable synthetic polymer (such as a polyarylate) or a non-synthetic material (such as collagen).

The physical characteristics of the implant may be modified by using different materials for the scaffold and/or forming the reinforcing matrix from fibers of different diameter, mechanical strength, stiffness, or durability. Moreover, the physical characteristics of the implant may be modified by cross-linking the scaffold, the reinforcing matrix or both. Cross-linking may be achieved by employing a variety of known methods including, but not limited to: chemical reaction with a carbodiimide, glutaraldehyde or formaldehyde among others; the application of energy such as radiant energy, which includes irradiation by UV light or microwave energy; dehydrothermal treatment in which water is slowly removed while the bone tissue is subjected to a vacuum; and enzymatic treatment.

A system and method for forming an implant with a reinforcing matrix will now be described with respect to FIGS. 5-9. Notably, the system and method are described herein in relation to the implant 100 of FIGS. 1-3. This discussion is sufficient for understanding the system and method for forming an implant 400 of FIGS. 4A-4C.

Figure 5:
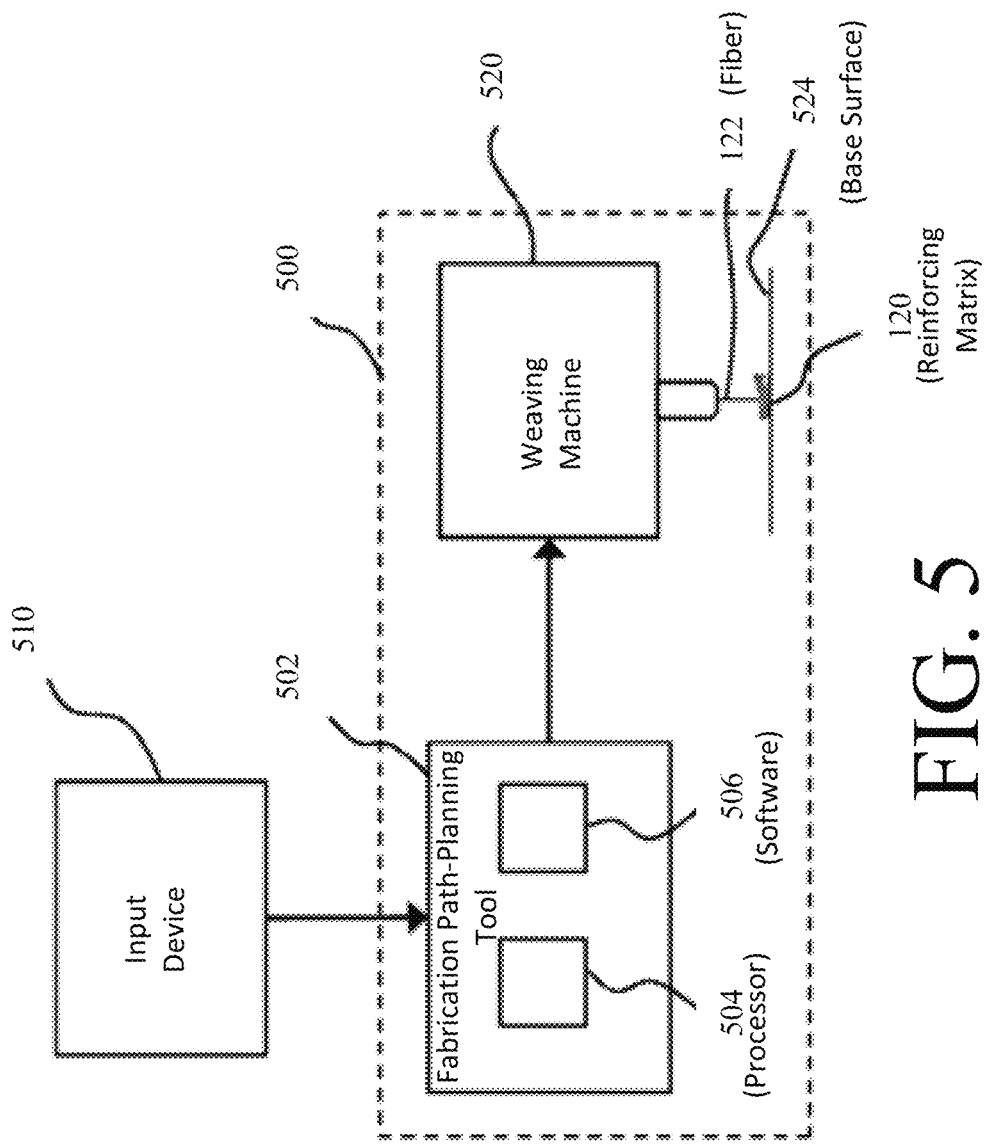
FIG. 5 is a schematic diagram of a system.
Figure 10:
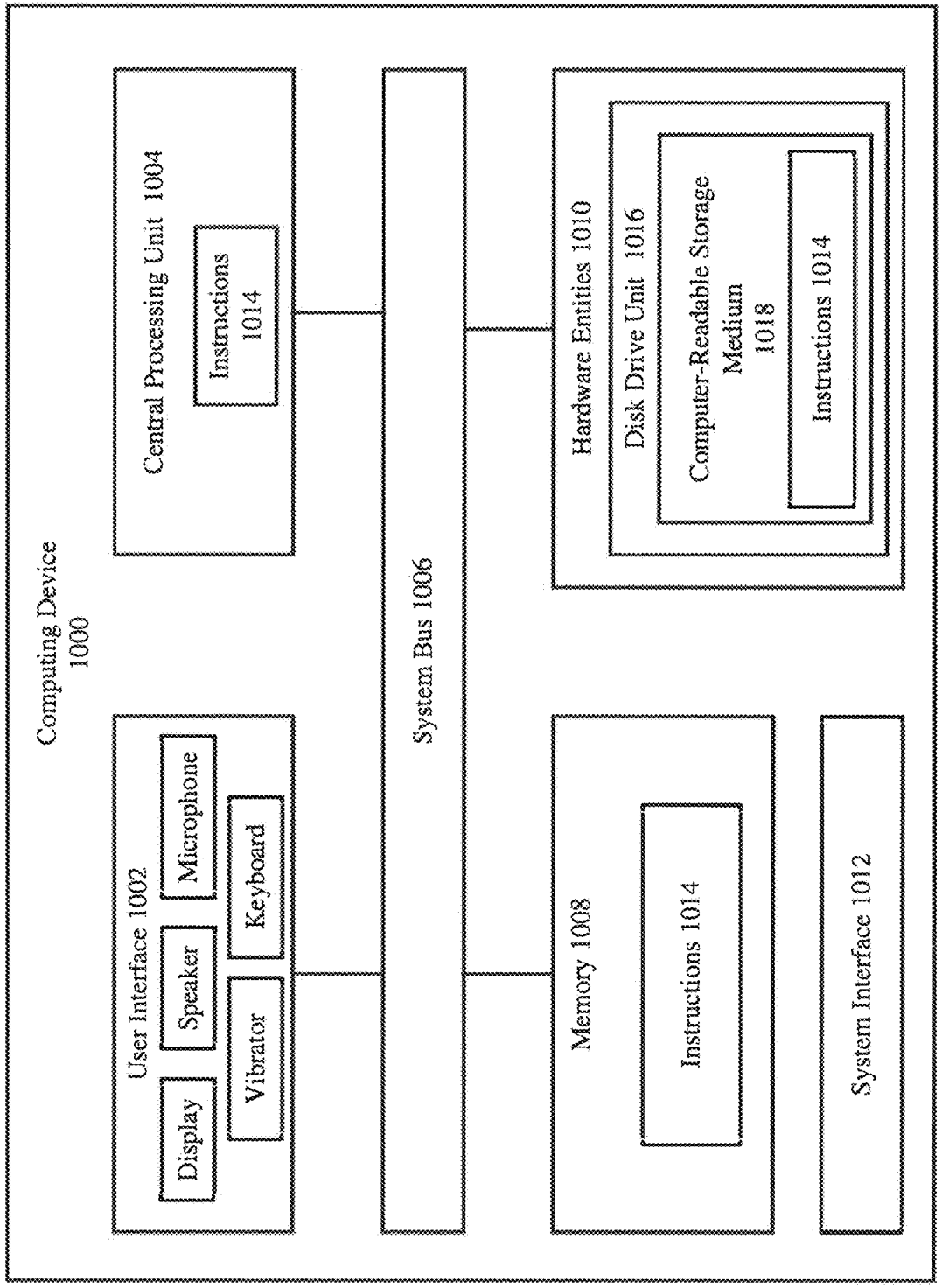
FIG. 10 is an illustration of an exemplary computing device.

Referring to FIG. 5, an exemplary system 500 is shown. The system 500 generally comprises a fabrication path-planning tool 502 and a weaving machine 520. The fabrication path-planning tool 502 includes a computing device. Computing devices are well known in the art, and therefore will not be described in detail herein. Still, an exemplary computing device 1000 is shown in FIG. 10. Computing device 1000 is described below.

As shown in FIG. 5, the fabrication path-planning tool 502 comprises at least a processor 504 configured to receive implant data from an input device 510. The input device 510 may be in the form of an image scanning device (e.g., a magnetic resonance imaging instrument (MRI), a nuclear imaging instrument, an ultrasound instrument or other imaging technology) configured to provide three-dimensional (3D) image data of the target tissue. In the event of input from an image scanning device, software 506 is provided for execution by processor 504. The software 506 includes instructions for causing processor 504 to reconstruct a 3D model of the native tissue (i.e., the meniscus from the non-injured knee) from the image data received from the image scanning device and then extract the articulating surface geometry of the tissue. Once the 3D model is created, the software 506 causes the processor 504 to derive the configuration of the intended reinforcing matrix 120. The determination may be made by doing a geometrical analysis of the 3D model relative to a large-scale knee MRI database. Alternative methods may also be utilized.

Alternatively, the input device 510 may be a manual input device (e.g., a keyboard), which allows the user to enter specific data associated with the target implant (e.g., left or right side of body, ML compartment width, AP compartment length, and whether there is a shift in symmetry to one side or the other). As a further alternative, the input device 510 may include both an image scanning device and a manual input.

Once the configuration of the intended implant is known (either via an image scanning device, manual input or a combination thereof), the software 506 causes the processor 504 to determine a "weaving path" of the weaving machine 520 to achieve the determined configuration of the reinforcing matrix 120. The weaving path will consist of a series of distinct weaving patterns at different height levels.

Figure 6A:
FIGS. 6A and 6B (collectively referred to as "FIG. 6") are perspective views of exemplary reinforcing matrices formed for a left knee meniscus implant and a right knee meniscus implant, respectively.
Figure 6B:

With reference to an exemplary planning of a weaving path for a meniscus implant, the software 506 (based on the determined or manually input implant data) causes the processor 504 to set the side of the body to a value of left or right, set the ML, set the AP, and set a pause time between each weaving step. Thereafter, the software 506 may cause the processor 504 to determine (either based on database lookup or manual input) the number of pins to be used in the weaving pattern, the symmetrical weight to be applied, and the number of inner and outer rounds within a weaving step. FIGS. 6A and 6B illustrate the distinct, asymmetrical weaving patterns of a left knee meniscus (FIG. 6A) versus a right knee meniscus (FIG. 6B).

From this information, the software 506 may cause the processor 504 to set the X radius to half of AP and the Y radius to half of the ML. With the input information, the software 506 causes the processor 504 to determine the arc length of outer pins and to adjust such based on the symmetrical weighting. With the arc length and number of pins known, the radial positions of the pins may be determined as an X and Y position of each pin in a 2D scenario (or additional a Z position in a 3D scenario). Additionally, in part based on whether the implant 100 is to be used on the left side or right side, the software 506 may cause the processor 504 to set the length (and thereby the X and Y position) for the anterior tail and posterior tail pins. With the pins located, the software 506 causes the processor 504 to determine the specific weaving pattern for each layer or weaving step.

Figure 7:
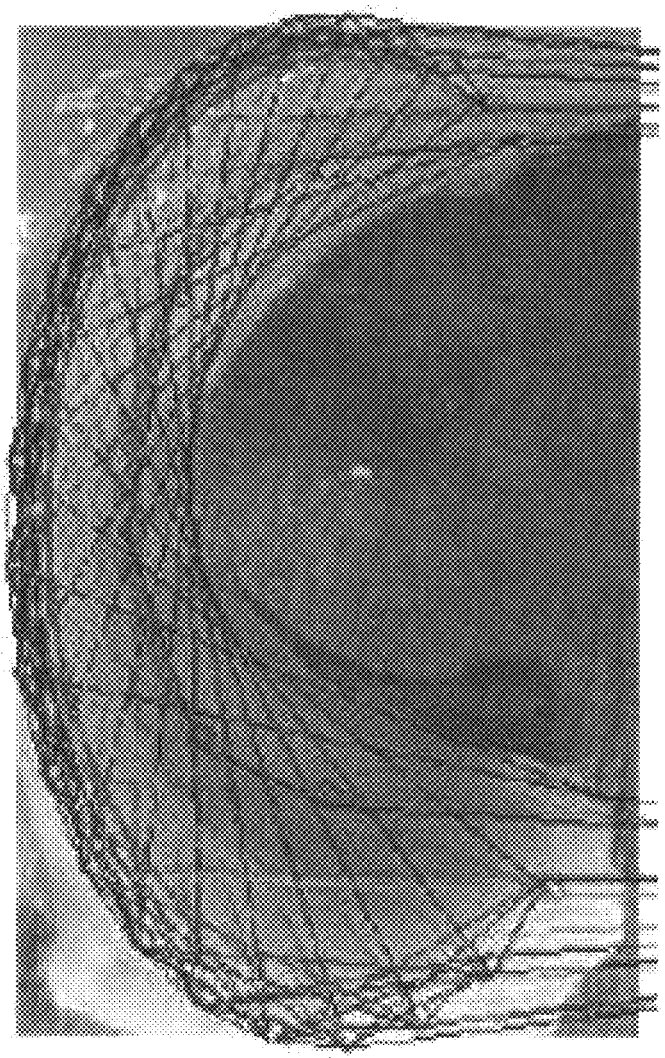
FIG. 7 is a perspective view illustrating a simulated planned weaving path superimposed over a meniscus.

Optionally, after the planned path is determined, the software 506 causes the processor 504 to conduct a simulation to verify that the weaving path can generate the intended articulating surface. As illustrated in FIG. 7, the simulated weaving pattern may be superimposed onto an image of the meniscus to verify the proper reinforcing matrix 120 is achieved. The software 506 may be further configured to cause the processor 504 to adjust the weaving pattern to achieve a proper reinforcing matrix 120 (e.g., by making the posterior region further thicker than the anterior region).

Once the planned weaving path has been determined, the data represented thereby may be provided from the processor 504 to the weaving machine 520. The weaving machine 520 may take various formats (e.g., a power loom or an additive manufacturing machine). In the scenario illustrated in FIG. 5, the weaving machine 520 applies the fiber 122 onto a base surface 524 about the pins to form the reinforcing matrix 120. As another alternative, a weaving machine may not be utilized and instead the reinforcing matrix may be woven by a user (e.g., by hand). In such case, the processor 504 may provide the planned weaving path to the user via another output device (e.g., a display or printer).

Figure 8A:
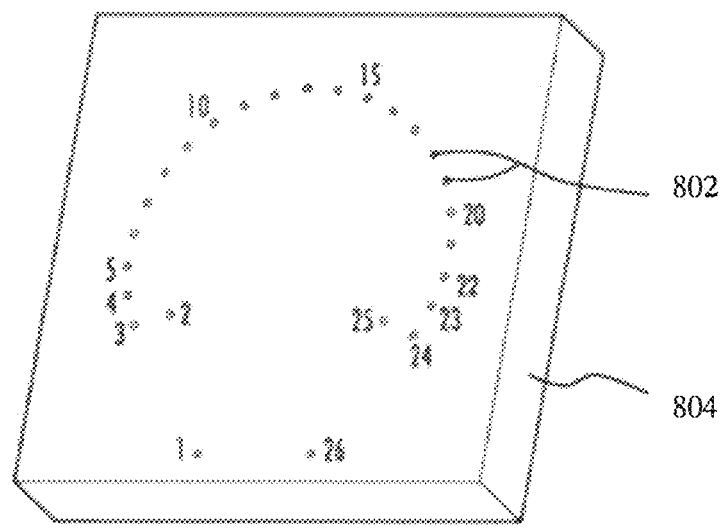
FIGS. 8A and 8B (collectively referred to as "FIG. 8") show a base plate pattern for fabrication of an exemplary meniscus reinforcing matrix.
Figure 8B:
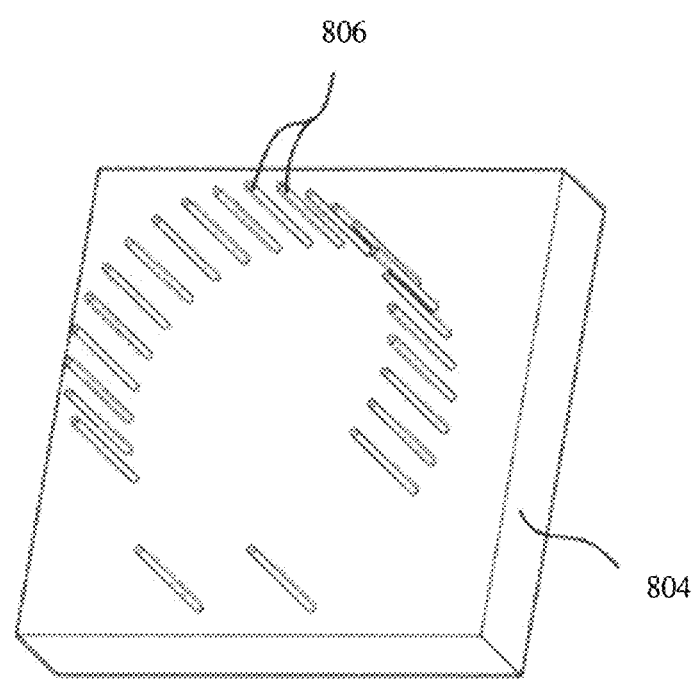
Figure 9:
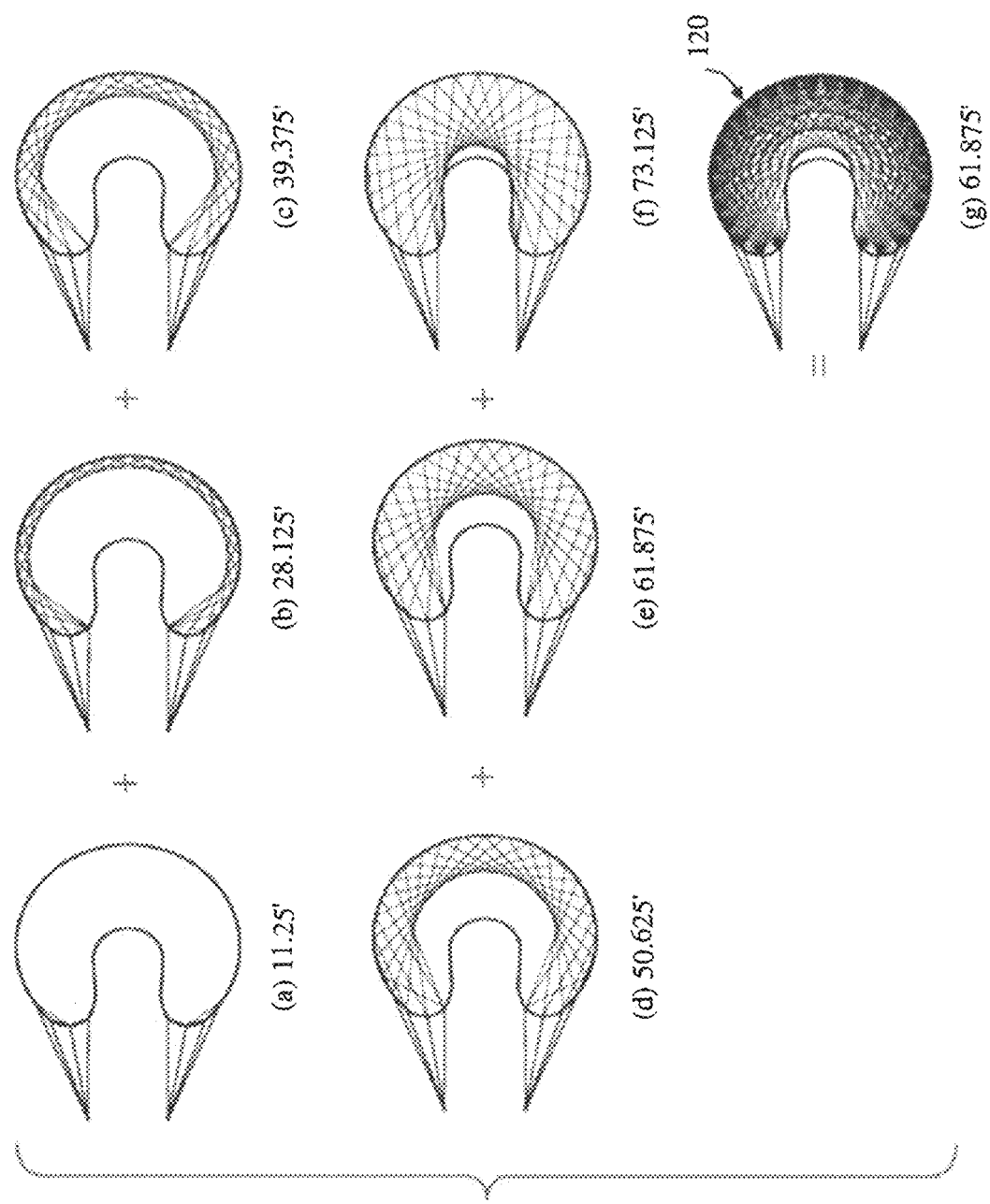
FIGS. 9(a), 9(b), 9(c), 9(d), 9(e), 9(f) and 9(g) (collectively referred to as "FIG. 9") show the organization of the reinforcing fibers during manufacture of the reinforcing matrix.

Referring to FIGS. 8-9, an exemplary forming process about pins (or pegs) 806 positioned on the base surface 524 will be described. The number of pins 806 is based on the determined planned path for the fiber 122. In the illustrated scenario, the base surface 524 includes twenty-four (24) holes 802 as shown in FIG. 8A. Twenty-two (22) holes 802 are at equal intervals forming a semi-circle with the remaining two (2) holes 802 opposite the center of the semi-circle. Pins 806 are positioned in the holes 802 forming the pattern shown in FIG. 8B. For purposes of explanation, each hole 802 of the base surface 524 is assigned a number from 1, 3-24 or 26. Holes 3 through 24 define the actual dimensions of the meniscus scaffold, while holes 1 and 26 define the anchor points for the scaffold.

Referring to FIGS. 9(a)-9(g), a continuous length of fiber 122 is dispensed from the weaving machine 520 and wrapped around the pins 806 in a quasi-circumferential pattern. Starting from point 1, fibers were wrapped and pivoted at one of six different off-tangent angles from the pins: (a) 11.25°, (b) 28.125°, (c) 39.375°, (d) 50.625°, (e) 61.875°, and (f) 73.125°. This continued until point 26, at which time the fiber was wrapped in reverse. For pins 3-6 and 21-24, fibers 23 were wrapped back to point 1 or 26 for formation of anchor bundles. This process was repeated for each angle to produce a complete pattern shown in FIG. 9(g). In accordance with the determined planned path, the pattern may be repeated several times. The pin pattern allows for a semi-lunar shape to be formed along with two (2) bundles of fibers at each horn for formation of the anchor plugs to form a meniscus implant. As explained above, implants with other shapes and configurations may also be formed. After wrapping has been completed, the fibers may be teased up (e.g., to form a wedge shaped cross-section) or otherwise treated.

To complete the implant 100, the reinforcing matrix 120 is inserted into a mold assembly (not shown) or a mold assembly is formed around the reinforcing matrix 120. The mold preferably has the same shape as the soft tissue in need of replacement. In some scenarios, the ends of the fiber forming the reinforcing matrix extend outside each end of the mold assembly to form the attachment points. The polymer or other material from which the scaffold 102 is to be manufactured is injected into the mold assembly to form the scaffold body 102, which is then solidified.

The process for solidifying the scaffold depends on the polymer used to form the scaffold. For example, if collagen is used, the implant assembly may be lyophilized. In some scenarios, the implant 100 may be cross-linked to alter its physical characteristics. Moreover, additives (such as proteins, glycosaminoglycans, cells, growth factors, medical agents, and/or labels, etc.) may be added to the implant 100 at any point during the fabrication thereof according to standard techniques known and used in the field.

As noted above, in some scenarios, both the fiber network matrix and the scaffold have same the shape and geometry as the soft tissue they are made to replace. For example, in implementations for the knee, the reinforcing matrix and the mold assembly may be constructed as a c-shaped disc with a wedge-like cross-section, similar to a knee meniscus.

Referring now to FIG. 10, there is provided a schematic illustration an exemplary computing device 1000. The computing device can include, but is not limited to, a personal computer, a laptop computer, a desktop computer and/or a server. The computing device 1000 is generally configured to perform operations for facilitating the generation of an implant (e.g., implant 100 of FIG. 1 or implant 400 of FIGS. 4A-4C). As such, the computing system 1000 comprises a plurality of components 1002-1012. The computing system 1000 can include more or less components than those shown in FIG. 10. However, the components shown are sufficient to disclose an illustrative embodiment implementing the present solution. Notably, the hardware shown in FIG. 10 can include physical hardware and/or virtual hardware.

The hardware architecture of FIG. 10 represents one (1) embodiment of a representative computing device configured to facilitate the generation of an implant (e.g., implant 100 of FIG. 1 or implant 400 of FIGS. 4A-4C). As such, the computing system 1000 implements methods of the present solution.

As shown in FIG. 10, the computing system 1000 includes a system interface 1012, a user interface 1002 (e.g., a keyboard for data input and a display for data output), a Central Processing Unit ("CPU") 1004, a system bus 1006, a memory 1008 connected to and accessible by other portions of the computing system 1000 through system bus 1006, and hardware entities 1010 connected to system bus 1006. System bus 1006 is also used to communicate one or more mission plans to and from the computing system 1000. At least some of the hardware entities 1010 perform actions involving access to and use of memory 1008, which can be a Random Access Memory ("RAM"), a disk driver and/or a Compact Disc Read Only Memory ("CD-ROM"). System interface 1012 allows the computing system 1000 to communicate directly or indirectly with external devices (e.g., sensors, servers and client computers).

Hardware entities 1010 can include microprocessors, Application Specific Integrated Circuits ("ASICs") and other hardware. Hardware entities 1010 can include a microprocessor programmed to facilitate the generation of an implant (e.g., implant 100 of FIG. 1 or implant 400 of FIGS. 4A-4C).

As shown in FIG. 10, the hardware entities 1010 can include a disk drive unit 1016 comprising a computer-readable storage medium 1018 on which is stored one or more sets of instructions (or programming instructions) 1014 (e.g., software code) configured to implement one or more of the methodologies, procedures, or functions described herein. The instructions 1014 can also reside, completely or at least partially, within the memory 1008 and/or the CPU 1004 during execution thereof by the computing device 1000. The components 1008 and 1004 also can constitute machine-readable media. The term "machine-readable media", as used here, refers to a single medium or multiple media (e.g., a centralized or distributed database, and/or associated caches and servers) that store the one or more sets of instructions 1014. The term "machine-readable media", as used here, also refers to any medium that is capable of storing, encoding or carrying a set of instructions 1014 for execution by the computing device 1000 and that cause the computing device 1000 to perform any one or more of the methodologies of the present disclosure.

Notably, the present solution can be implemented in a single computing device as shown in FIG. 10. The present solution is not limited in this regard. Alternatively, the present solution can be implemented in a distributed network system. For example, the present solution can take advantage of multiple CPU cores over a distributed network of computing devices in a cloud or cloud-like environment. The distributed network architecture ensures that the computing time of the statistics and enhanced functionality is reduced to a minimum, allowing end-users to perform more queries and to receive reports at a faster rate. The distributed network architecture also ensures that the implementing software is ready for being deployed on an organization's internal servers or on cloud services in order to take advantage of its scaling abilities (e.g., request more or less CPU cores dynamically as a function of the quantity of data to process or the number of parameters to evaluate).

The following EXAMPLE is provided in order to further illustrate the present solution. The scope of the present solution, however, is not to be considered limited in any way thereby.

EXAMPLE

Initial Symmetric Weaving

In one case, a computing device was configured to determine pin placement and pattern weaving. In this regard, the computing device first took two (2) primary dimensions: an Anterior-to-Posterior (AP) length; and a Medial-to-Lateral (ML) width. Based on these dimensions (obtained from X-ray, MRI, CT or predictive modeling), an ellipse was constructed with n nodes equally spaced around the circumference from +225 degrees (left) to −45 degrees (right).

Figure 11:
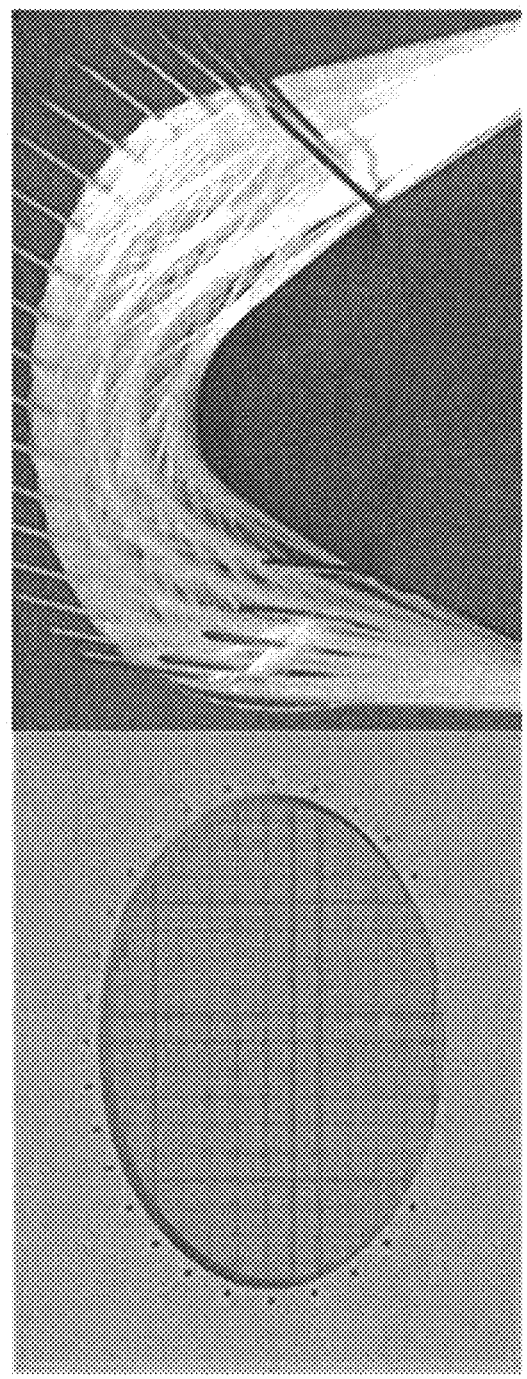
FIGS. 11(a) and 11(b) (collectively referred to as "FIG. 11") provide illustrations that are useful for understanding how an implant is fabricated.

As shown in FIG. 11(a), twenty-five (25) nodes were used which have a spacing of 11.25 degrees. This approach is adapted from initial ovine studies (AP: 26 mm, ML: 20 mm) and scaled up (AP: 45 mm, ML: 32 mm). During fabrication of an implant, a platform with holes at the specified locations was constructed. Pins were placed through the holes. A scaffold was fabricated using an 86-pattern weave as shown in FIG. 11(b). The dimensions of the resulting implant were slightly greater (<5%) than the original ellipse due to wound fiber around the outside of pins, but still within an acceptable tolerance.

Root Location Nodes

In order to achieve a more anatomically accurate implant, the end node locations (i.e., Node 1 and Node 25 with 25 nodes) were more accurately defined based on MRI measurements or average historical data. Thus, for n nodes, theta varies according to the following Mathematical Equation (1).

$$\Theta(x) = \Theta(x-1) + \frac{\Theta(n) - \Theta(1)}{n-1} \qquad (1)$$

where $\theta(x)$ represents an $x^{th}$ angle, $\theta(x-1)$ represents a previous adjacent angle, $\theta(n)-\theta(1)$ represents a total angular distance from a first node to a last node, and n−1 represents a number of gaps (one less than the number of nodes n).

Figure 12:
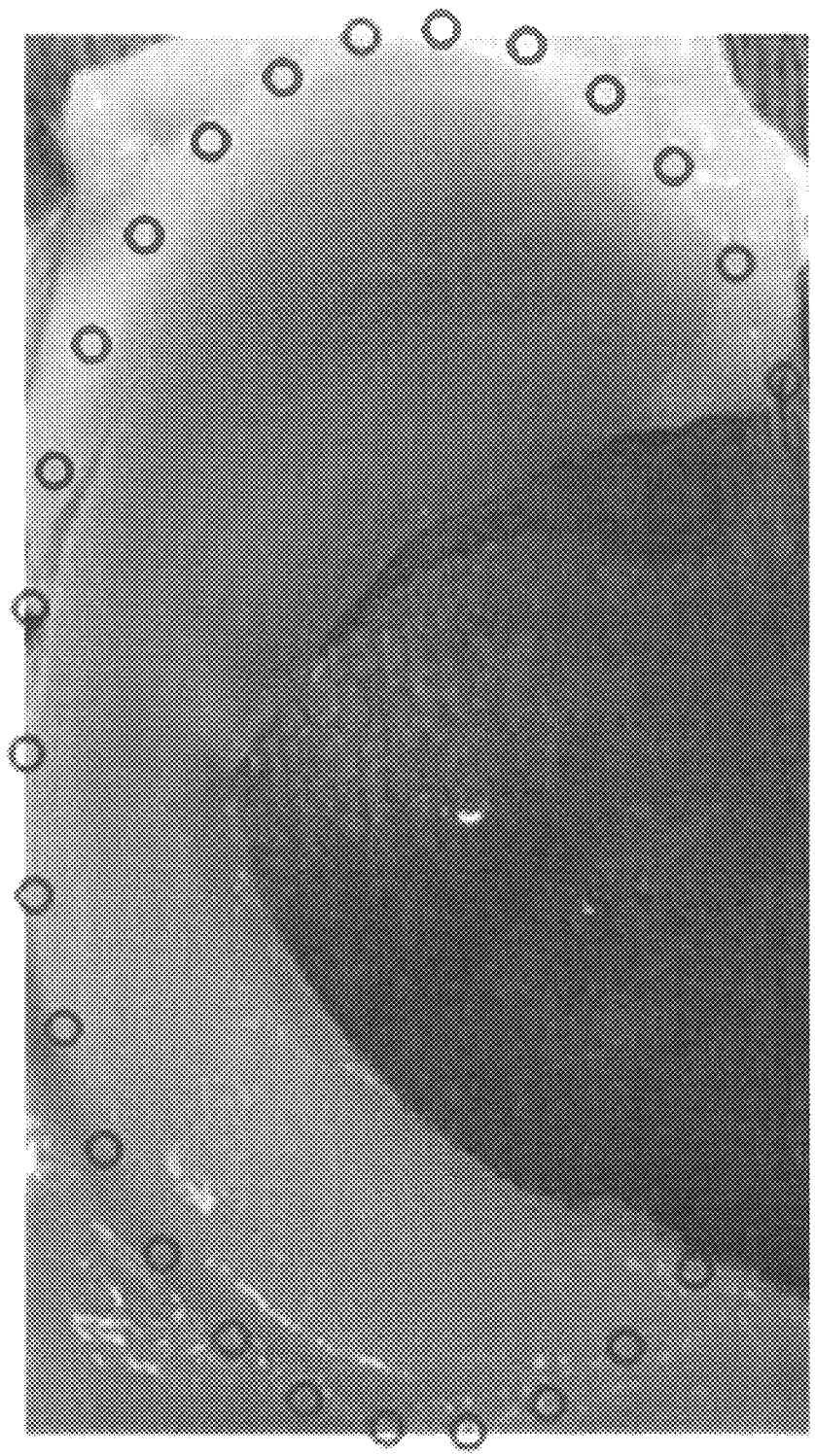
FIG. 12 provides an illustration of an exemplary ellipse (created using anterior-to-posterior and medial-to-lateral dimensions of cadaveric meniscus) that accurately recreates outer meniscal rim and meniscal root placements (anterior on left, posterior on right).

In this EXAMPLE, images were taken of human cadaveric medial menisci. Based on these images, roots were placed at 220 degrees and −60 degrees. As shown in FIG. 12, an ellipse (created using AP and ML dimensions of cadaveric meniscus) accurately recreated the outer meniscal rim and meniscal root placements (anterior on left, posterior on right).

Asymmetry Pin Arrangements

In order to also account for differences in anterior, body, and posterior widths, the spacing between nodes was varied. This spacing variation was achieved by rewriting Mathematical Equation (1) as Mathematical Equation (2) including a third term. The third term ensures that the spacing between nodes (or pins) n can be changed using a weighting factor W.

$$\Theta(x) = \Theta(x-1) + \frac{\Theta(n) - \Theta(1)}{n-1} - W*\left(\frac{n}{2} - x + 1\right) \quad (2)$$

The weighting factor W ranges from zero (0) to one (1), with zero (0) being symmetrical and one (1) being very asymmetrical.

Figure 13:
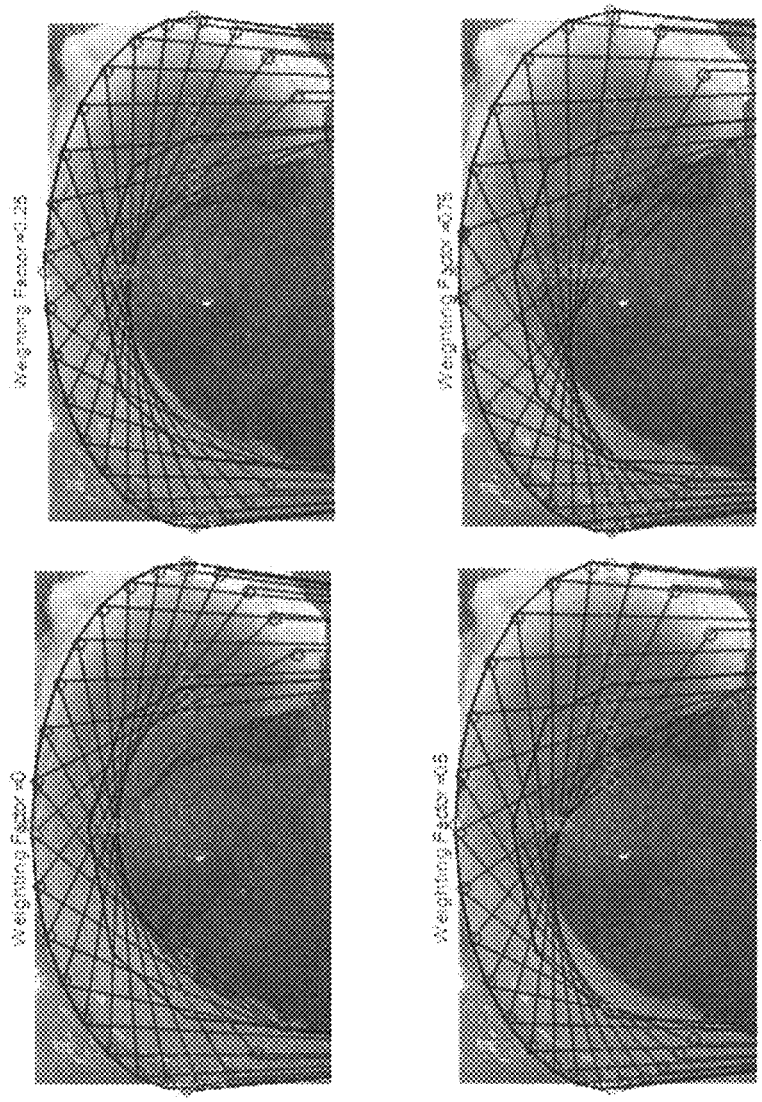
FIG. 13 provides illustrations that are useful for understanding how a weighting factor W=0.25 may approximate a given image of a cadaveric medial meniscus.

Using the base pattern of a meniscus scaffold design, it becomes evident how varying the weighting factor W can greatly change the asymmetry of the scaffold and close in on a more anatomically accurate design. From FIG. 13, it appears that a weighting factor W=0.25 approximates a given image of a cadaveric medial meniscus.

Weighting Factor Optimization

Figure 14:
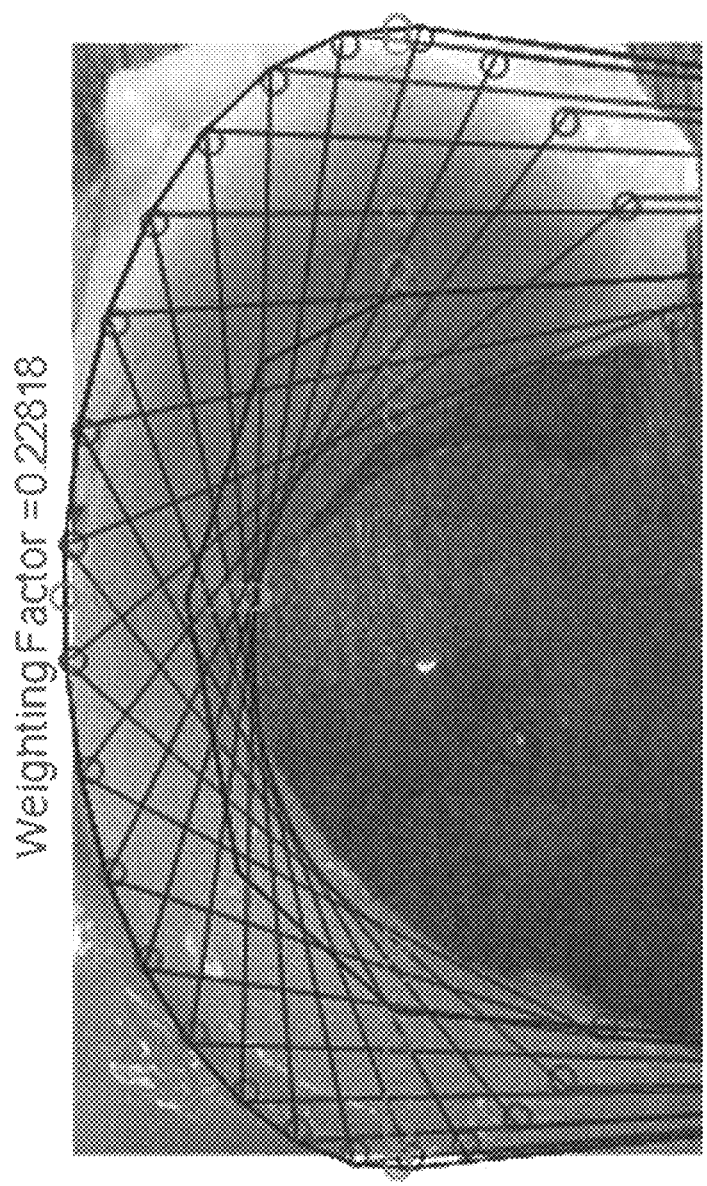
FIG. 14 is an illustration showing how patient specific menisci is fabricated using a weighting factor of 0.228.

Furthermore, if specific anterior, body, and posterior dimensions are given for a desired meniscus based on MM or historical data, the weighting factor W for each implant can be optimized. Average anterior ("ANT"), body ("BOD") and posterior ("POS") widths from literature were typically 8.68, 9.14 and 14.26, respectively. The weighting factor W that minimizes the root-mean-square error between desired implant widths and actual implant widths in the three (3) regions was found and can be found if a patient's anterior, body, and posterior widths are available. The root-mean-square computations can be defined by the following the Mathematical Equation (3).

$$RMSError = \quad (3)$$
$$\sqrt{(ANT_{des} - ANT_{act})^2 + (BOD_{des} - BOD_{act})^2 + (POS_{des} - POS_{act})^2}$$

where RMSError represents a root-mean-square error, $ANT_{des}$ represents a desired anterior width, $ANT_{act}$ represents an actual anterior width, $BOD_{des}$ represents a desired body width, $BOD_{act}$ represents an actual body width, $POS_{des}$ represents a desired posterior width, and $POS_{act}$ represents an actual posterior width. With an average AP of 41.38 mm, an average ML of 30.63 mm, and the above listed typical anterior, body and posterior widths, a weighting factor W of 0.228 was found to minimize the overall error between the three (3) regions. This weighting factor W of 0.228 can then used to fabricate patient specific menisci, as shown in FIG. 14.

Based on Mill- or historical data-derived dimensions of AP, ML, Ant, BOD, POS, the node placement and weighting factor W can be optimized to minimize error in the final dimensions.

Node/Pattern Variations

Figure 15:
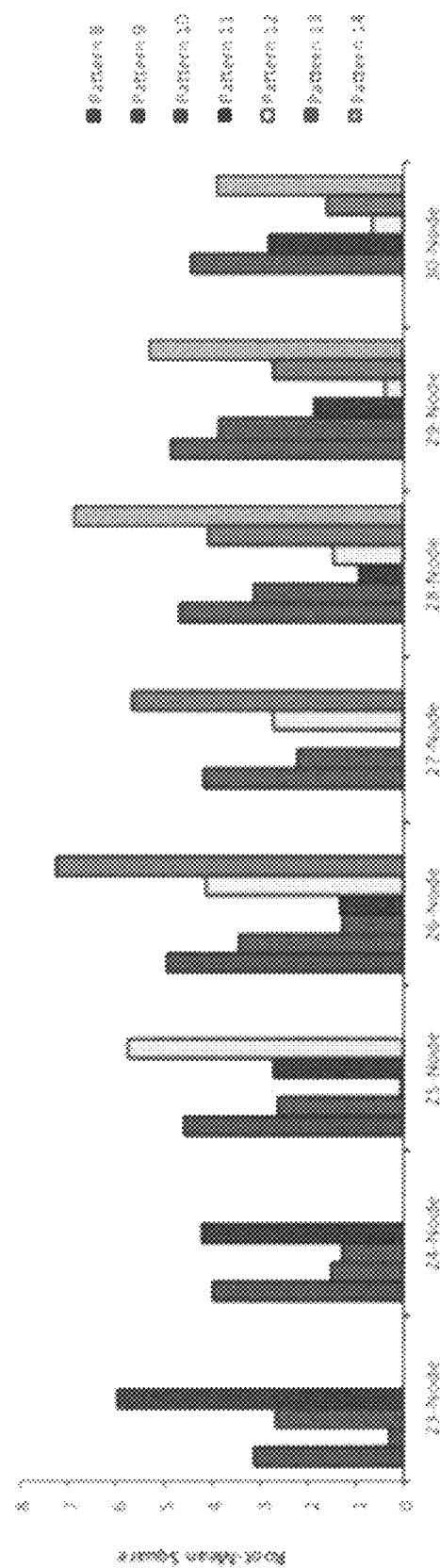
FIG. 15 is a graph that is useful for understanding best node-pattern combinations in a given scenario.

The above simulations were performed using twenty-five (25) nodes and a base pattern that skipped ten (10) nodes per weave (Pattern 10). However, varying the number of nodes and pattern number (nodes skipped) can provide other options to minimize the root-mean-square error. Thus, twenty-three (23) to thirty (30) nodes were attempted, varying the pattern number from eight (8) to fourteen (14). For each combination, following weighting factor optimization, the root-mean-square error was recorded. The resulting errors are shown in FIG. 15. The following were the best node-pattern combinations.

23-Node, Pattern 9
25-Node, Pattern 10
27-Node, Pattern 11
29-Node, Pattern 12

These combinations can be attempted by the code for each specific patient's dimensions, and thus would change based upon the required scaffold design.

Patient/Donor-Specific Menisci

Based on statistical approaches, a person's height, weight, and gender can be used to accurately predict their menisci's AP and ML dimensions. Thus, three (3) cadaveric knee specimens and the donor information were obtained from the Robert Wood Johnson Medical School Anatomical Association. Based on the information, AP and ML dimensions were calculated, allowing for node placement with a weighting factor W of 0.228. Platforms with these nodes were constructed, and donor-specific implants were fabricated as shown in the left image of FIG. 16. The scaffolds were fabricated with an anterior tail of 30 mm and posterior tail of 50 mm to aid in our approach to surgical fixation. These tail lengths could be easily altered for the desired fixation technique. Following fabrication, dimensions were comparable to those obtained with the computer program. In addition, all five (5) dimensions (AP, ML, anterior, body, posterior widths) were within ten percent (10%) of the native meniscus values.

Figure 16:
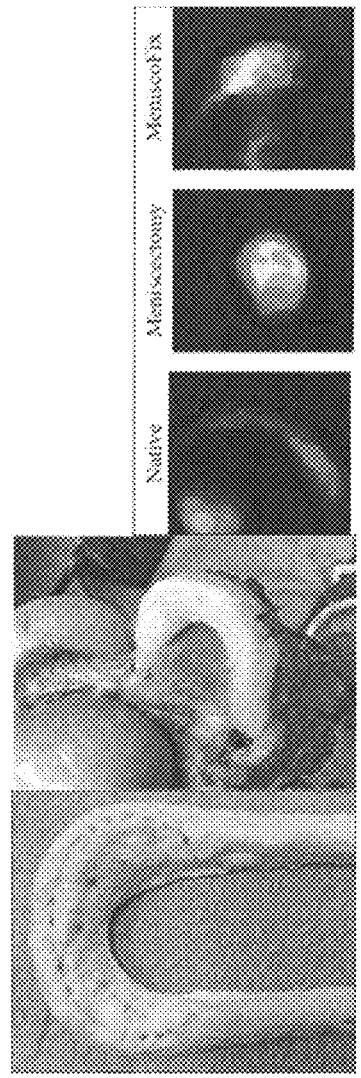
FIG. 16 provides images that are useful for understanding how donor-specific implants are fabricated in accordance with the present solution.

Additionally, devices were implanted into cadaveric knees (as shown in FIG. 16—middle image) and the load-distributing properties were characterized with a Tekscan strip (as shown in FIG. 16—right image). The implanted devices improved load-distributing properties over meniscectomy with some similarities to native, and no issues with implant sizing were noted.

Figure 17:
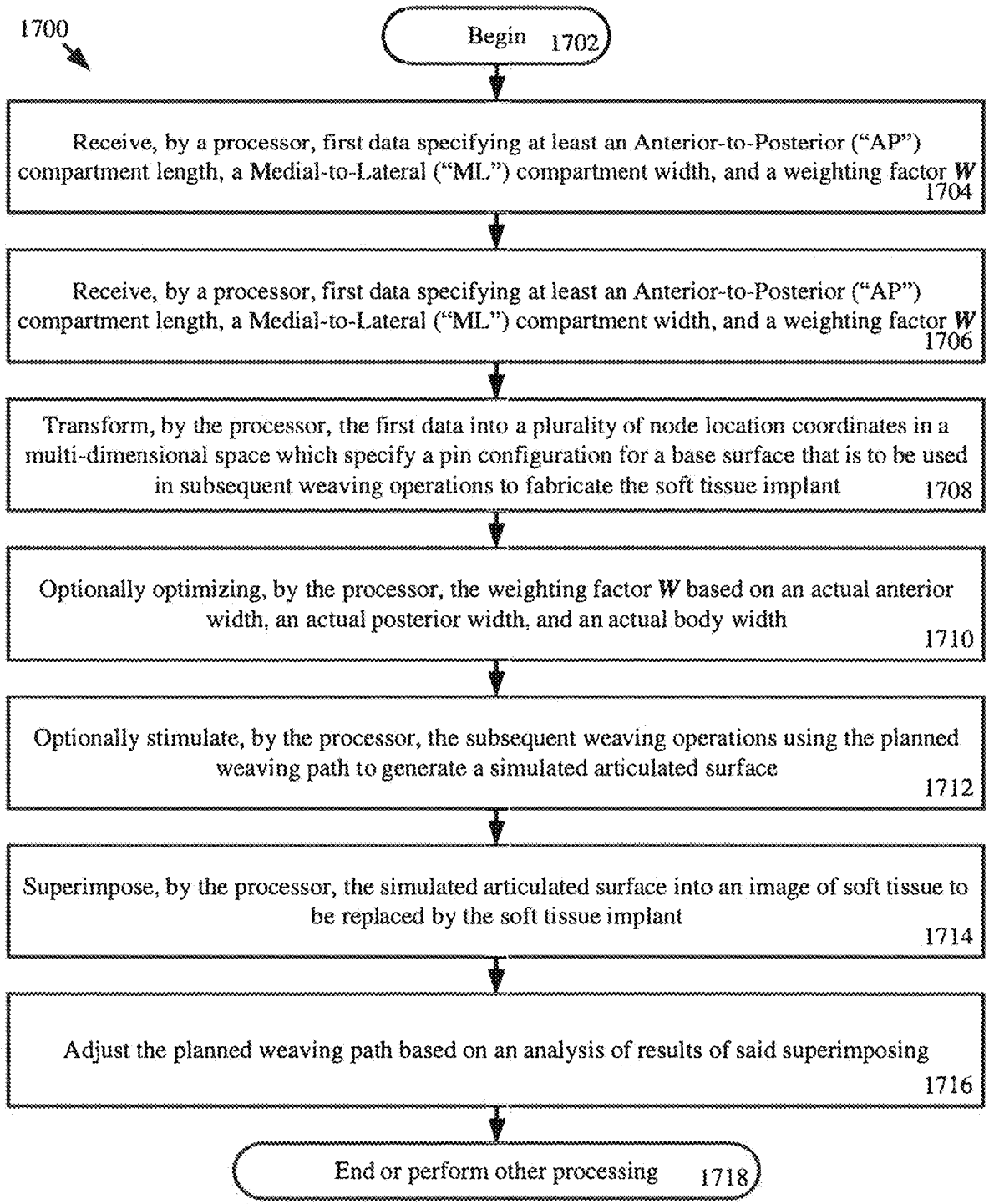
FIG. 17 is a flow diagram of an exemplary method for fabricating a soft tissue implant in accordance with the present solution.

Referring now to FIG. 17, there is provided a flow diagram of an exemplary method 1700 for fabricating a soft tissue (e.g., a fibrocartilage tissue) implant (e.g., implant 100 of FIG. 1 or 400 of FIG. 4). Method 1700 can be implemented by system 500 of FIG. 5 and/or computing device 1000 of FIG. 10. Method 1700 begins with 1702 and continues with 1704 where a processor (e.g., processor 504 of FIG. 5 and/or CPU 1004 of FIG. 10) receives first data specifying at least an AP compartment length, an ML compartment width, and a weighting factor W. Next in 1706, the processor uses the first data to generate second data defining a target soft tissue implant. The target soft tissue implant comprises a scaffold (e.g., scaffold 102 of FIG. 1 or scaffold 402 of FIG. 4) designed to replace a biological soft tissue in a subject and a reinforcing matrix (e.g., reinforcing matrix 120 of FIG. 1 or matrix 404 of FIG. 4) designed to provide structural support to the scaffold. The processor then uses the plurality of node locations in 1708 to determine a planned weaving path for forming an interlaced fibrous structure having a shape based on a shape of the target soft tissue implant. Information defining the planned weaving path is communicated from the processor to an external output device (e.g., weaving machine 520 of FIG. 5) for facilitating performance of the subsequent weaving operations resulting in the fabrication of the soft tissue implant. In some scenarios, the external output device is a weaving machine which forms the interlaced fibrous structure in accordance with the planned weaving path. Alternatively or additionally, the external output device is a display or printer (as shown in box 1002 of FIG. 10).

Upon completing 1708, optional operation 1710 is performed for optimizing the weighting factor W based on an actual anterior width, an actual posterior width, and an actual body width. The weighting factor W is optimized using a root-mean-square error algorithm to identify a value that minimized an error between desired implant widths and actual implant widths in an anterior region, a posterior region and a body region. The root-mean-square error algorithm is defined by the above specified Mathematical Equation (3). Method 1700 may also optionally involve: simulating the subsequent weaving operations using the planned weaving path to generate a simulated articulating surface (as shown by 1712); superimposing the simulated articulated surface into an image of soft tissue to be replaced by the soft tissue implant (as shown by 1714); and adjusting the planned weaving path based on an analysis of results of said superimposing (as shown by 1716). Subsequently, 1718 is performed where method 1700 ends or other processing is performed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the following claims.

What is claimed is:

1. An implant fabricated by:
receiving, by a processor, first data specifying at least a tissue dimension and a weighting factor W;
optimizing the weighting factor W based on at least one an actual anterior width, an actual posterior width, and an actual body width, the optimizing comprising using a root-mean-square error algorithm to identify a value that minimizes an error between desired implant widths and actual implant widths in an anterior region, a posterior region and a body region;
using, by the processor, the first data to generate second data defining the implant, the implant comprising a scaffold designed to replace a biological tissue in a subject and a reinforcing matrix designed to provide structural support to the scaffold;
transforming, by the processor, the first data into a plurality of node location coordinates in a multi-dimensional space which specify a node configuration for a base surface used in subsequent weaving operations to fabricate the implant;
using, by the processor, the plurality of node locations to determine a planned weaving or printing path for forming an interlaced fibrous structure having a shape based on a shape of the implant; and
communicating information defining the planned weaving or printing path from the processor to an external output device for facilitating performance of the subsequent weaving or printing operations resulting in the fabrication of the implant.

2. The implant of claim 1, wherein fabrication of the implant further comprises injecting a scaffold material into the interlaced fibrous structure to form the implant.

3. The implant of claim 1, wherein the tissue comprises a fibrocartilage tissue and the tissue dimension comprises at least one of an Anterior-to-Posterior ("AP") compartment length and a Medial-to-Lateral ("ML") compartment width.

4. The implant of claim 1, wherein the external output device is a weaving machine which forms the interlaced fibrous structure in accordance with the planned weaving path.

5. The implant of claim 1, wherein fabrication of the implant further comprises:
forming an anterior attachment point by a first fiber of the interlaced fibrous structure that exits from an anterior end of the scaffold; and
forming a posterior attachment point by a second fiber of the interlaced fibrous structure that exits from a posterior end of the scaffold,
wherein the anterior attachment point and the posterior attachment point are configured for attachment of the implant to surrounding tissue.

6. The implant of claim 5, wherein the first fiber and the second fiber have different lengths.

7. The implant of claim 1, wherein the weighting factor W is optimized to introduce asymmetry into a shape of the implant.

8. The implant of claim 1, wherein the weighting factor W alters a spacing between the node location coordinates to introduce asymmetry into a shape of the implant.

9. The implant of claim 1, wherein using the root-mean-square error algorithm to identify the value that minimizes the error between desired implant widths and actual implant widths in the anterior region, the posterior region and the body region comprises performing at least one of the following:
skipping one or more of the plurality of node locations during the subsequent weaving or printing operations; or
selecting, from a database, a weaving pattern that minimize the error.

10. The implant of claim 1, wherein determining the planned weaving or printing path for forming the interlaced fibrous structure comprises selecting, from a database, an asymmetrical weaving pattern when the implant is configured to replace a knee meniscus.

11. The implant of claim 1, wherein fabrication of the implant further comprises simulating the subsequent weaving operations using the planned weaving path to generate a simulated articulating surface.

12. The implant of claim 11, wherein fabrication of the implant further comprises superimposing the simulated articulated surface into an image of soft tissue to be replaced by the soft tissue implant.

13. The implant of claim 11, wherein fabrication of the implant further comprises adjusting the planned weaving path based on an analysis of results of said superimposing.

14. The implant of claim 1, wherein the implant is a meniscal replacement device.

15. The implant of claim 1, wherein the implant is an intervertebral disc replacement device.

16. An implant fabricated by:
receiving first data specifying at least a tissue dimension and a weighting factor W, the weighting factor W being optimized based on at least one an actual anterior width, an actual posterior width, and an actual body width, the optimizing comprising using a root-mean-square error algorithm to identify a value that minimizes an error between desired implant widths and actual implant widths in an anterior region, a posterior region and a body region;
using the first data to generate second data defining the implant, the second data comprising a reinforcing matrix formed from an interlaced fibrous structure and designed to provide structural support to a scaffold;
transforming the first data into a plurality of node location coordinates in a multi-dimensional space which specify a node configuration for a base surface used in subsequent weaving operations for forming the interlaced fibrous structure, the interlaced fibrous structure having a shape corresponding to a shape of the implant;

using the plurality of node locations to determine a planned weaving or printing path for forming the interlaced fibrous structure; and communicating information defining the planned weaving or printing path to an external output device for facilitating performance of the subsequent weaving or printing operations resulting in the fabrication of the interlaced fibrous structure.

17. The implant of claim 16, wherein fabrication of the implant further comprises injecting a scaffold material into the fabricated interlaced fibrous structure to form the implant.

18. The implant of claim 16, wherein the weighting factor W is optimized to introduce asymmetry into a shape of the implant.

19. The implant of claim 16, wherein the weighting factor W alters a spacing between the node location coordinates to introduce asymmetry into a shape of the implant.

* * * * *